United States Patent [19]
Fishbine et al.

[11] Patent Number: 5,222,152
[45] Date of Patent: Jun. 22, 1993

[54] PORTABLE FINGERPRINT SCANNING APPARATUS FOR IDENTIFICATION VERIFICATION

[75] Inventors: Glenn M. Fishbine, Eden Prairie; Robert J. Withoff, Minnetonka, both of Minn.

[73] Assignee: Digital Biometrics, Inc., Minnetonka, Minn.

[21] Appl. No.: 794,476

[22] Filed: Nov. 19, 1991

[51] Int. Cl.$^5$ ............................................. G06K 9/00
[52] U.S. Cl. ........................................ 382/2; 356/71; 340/825.34; 382/4
[58] Field of Search ............... 382/4, 5, 2; 358/93, 358/108; 356/71; 340/825.3, 825.31, 825.34

[56] References Cited
U.S. PATENT DOCUMENTS 4,210,899 7/1980 Swonger et al. .................. 382/5
4,449,189 5/1984 Feix et al. .......................... 382/2
4,843,377 6/1989 Fuller et al. ........................ 382/4

Primary Examiner—Leo H. Boudreau
Attorney, Agent, or Firm—Merchant, Gould, Smith, Edell, Welter & Schmidt

[57] ABSTRACT

A portable fingerprint scanning apparatus for identification verification which can optically scan and record fingerprint images in the field and wirelessly transmit said images to a mobile unit for processing and subsequent wireless transmission to a central location for the purpose of providing immediate identity and background checks on the individual being fingerprinted. The apparatus includes a fingerprint scanner and a wireless transmitter to transmit the fingerprint image to a mobile unit. The apparatus can also include a video camera to capture a photographic image or "mug shot" for wireless transmission to a mobile unit.

22 Claims, 2 Drawing Sheets

PORTABLE FINGERPRINT SCANNING APPARATUS FOR IDENTIFICATION VERIFICATION

BACKGROUND OF THE INVENTION

1. Field of the Invention

The present invention relates to apparatus for the live scanning of fingerprint images and more particularly to a portable apparatus for the scanning and capture of fingerprint images and the wireless transmission of said images to a central location for identity verification.

2. Description of Background Material

Over the years, the most commonly used techniques for both identity verification and the identification of potential crime suspects have been the use of fingerprints and photographs or "mug shots".

Originally, fingerprinting was done by inking a suspect's finger and applying the inked finger to paper. As can be readily understood, fingerprint information in this form was difficult to use. Making a fingerprint match was an extremely time-consuming task. Digital technology significantly advanced the art of fingerprinting. Inked images could be scanned, the image digitalized and recorded in a manner that could later be searched in a reasonably expeditious manner by computer. Problems arose, however, due to the quality of inked images. Over- and under-inking resulted in blurred or vague images, thus rendering the digitalized information useless. Further, the process of scanning an inked image was relatively time consuming.

These and other problems led to "live scanning". According to live scanning techniques, the fingerprint of a suspect is scanned directly from the suspect's finger, as opposed to being scanned from an inked image of the print. More specifically, live scans are those procedures which capture fingerprint ridge detail in a manner which allows for the immediate processing of the fingerprint image with a computer. Original work in the field dates back to original patents filed in 1964 concerning techniques used to capture high contrast images of fingerprint for photographic or digital capture of fingerprints.

Since their introduction, live scans have become an important tool for law-enforcement. The live scan has the potential to overcome inherent weaknesses in the ink capture of fingerprints and provide immediate transmission of fingerprint images; and allow for image enhancement if necessary.

These characteristics provide law-enforcement with the ability to improve the quality of the fingerprint data base, thereby improving the likelihood that identifications can be made either from latent fingerprints or from identity verification checks. In addition, live scan fingerprints are easily adaptable to computerized storage and processing techniques, increasing cooperation and fingerprint data transfer between various police agencies.

Systems which optically or optically and mechanically generate fingerprint images are in use. Several such fingerprinting systems are disclosed in Fishbine et al., U.S. Pat. Nos. 4,811,414 and 4,933,976; Ruell German Patent No. 3423886 A1; Becker U.S. Pat. No. 3,482,498; McMahon U.S. Pat. No. 3,975,711; Schiller U.S. Pat. Nos. 4,544,267 and 4,322,163; Marcus U.S. Pat. No. 4,533,837 and White U.S. Pat. No. 3,200,704.

While the fingerprinting systems disclosed in the foregoing patents are capable of providing optical or optical and mechanical fingerprint images, said systems are only suitable for use at a central location such as the police station. It is evident that there is also a need for a portable and lightweight fingerprint scanning system which can optically generate fingerprint images in the field. Such a portable system would be ideal for traffic officers and other law enforcement professionals who want to perform an immediate identity and background check on an individual while in the field. It is also evident that there is a need for a portable fingerprint system which has the capability for the wireless transmission of fingerprint images captured in the field to a central facility for identity verification using an automated fingerprint identification system.

It is further evident that there is a need for a portable fingerprint system which also includes the capability of capturing a photographic image or "mug shot" for wireless transmission to a central facility for identity verification using systems such as the FBI National Crime Information Center Network.

SUMMARY OF THE INVENTION

The present invention is a portable and lightweight fingerprint scanning apparatus which can optically scan and record fingerprint images in the field and wirelessly transmit said images to a mobile unit for processing and subsequent wireless transmission to a central location for the purpose of providing immediate identity and background checks on the individual being fingerprinted. The apparatus of the present invention includes a fingerprint scanner and a wireless transmitter to transmit the fingerprint image to a mobile unit. In the preferred embodiment the present invention also provides for the capability of using a video camera to capture a photographic image or "mug shot" for wireless transmission to a mobile unit. An especially preferred embodiment of the present invention also provides the ability to preview the fingerprint and "mug shot" images on a video monitor and to control transmission and processing of the fingerprint and "mug shot" images by the mobile unit using a terminal or keypad located on the portable fingerprint scanning apparatus. The present invention allows law enforcement professionals to perform immediate identity and background checks on an individual while in the field.

DETAILED DESCRIPTION OF THE PREFERRED EMBODIMENTS

In the following Detailed Description of the Preferred Embodiments, reference is made to the accompanying Drawings which form a part hereof, and in which is shown by way of illustration specific embodiments in which the invention may be practiced. It is to be understood that the other embodiments may be utilized and structural changes may be made without departing from the scope of the present invention.

Figure 1:
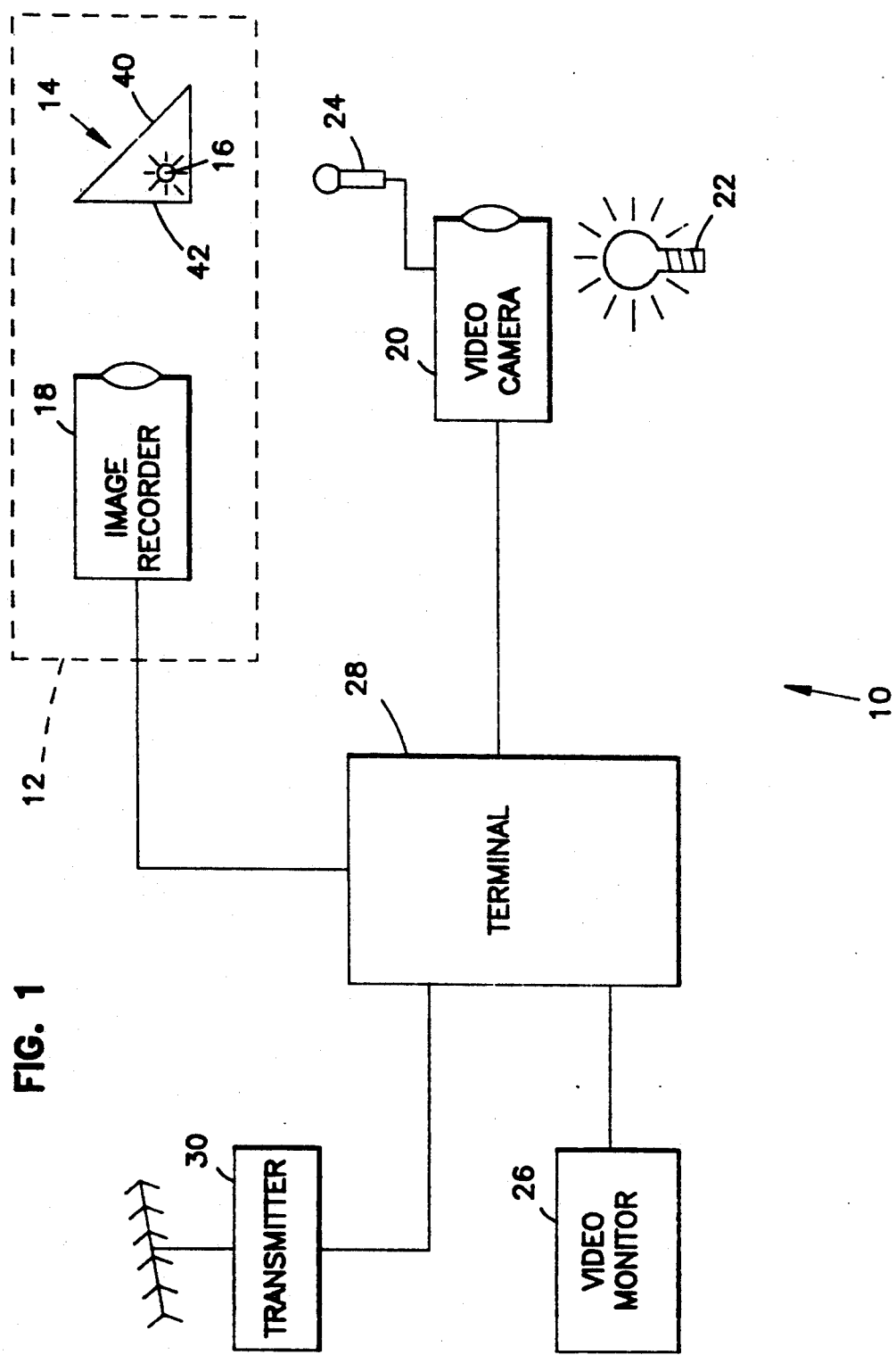
FIG. 1 is a block diagram representation of an apparatus which can be used to capture fingerprint and photographic images in the field and transmit said images via wireless transmission to a central location for identification verification in accordance with the present invention.

A portable identification verification system 10 which can be used to optically capture and produce fingerprint images in accordance with the present invention is illustrated generally in FIG. 1. Portable identification verification system 10 includes fingerprint scanner 12, video camera 20, video monitor 26, and transmitter 30 all interfaced to terminal 28. Terminal 28 includes a keyboard (not separately shown) which is used by an operator to interface with portable identification verification system 10. Fingerprint scanner 12 consists of a finger prism 14 and an image recorder 18. Fingerprint images from the portion of a finger placed in contact with receiving surface 40 of finger prism 14 are imaged by image recorder 18. Image recorder 18 will include a lens and shutter mechanism (not separately shown). Fingerprint images generated by fingerprint scanner 12 can be displayed on video monitor 26 and transmitted by transmitter 30 to a mobile unit (not separately shown) for further processing. Video camera 20 generates a video image, or "mug shot", of the person being fingerprinted. The video image generated by video camera 20 can be displayed on the video monitor 26 and transmitted by wireless transmitter 30 to a mobile unit (not separately shown) for viewing or recording. Terminal 28 controls whether the image from fingerprint scanner 12 or video camera 20 is displayed on video monitor 26. Terminal 28 also controls whether the image from fingerprint scanner 12 or video camera 20 is transmitted by wireless transmitter 30 to the mobile unit. Terminal 28 also transmits control signals via wireless transmitter 30 to the mobile unit to initiate processing and digitizing of the images in the mobile unit.

Figure 2:
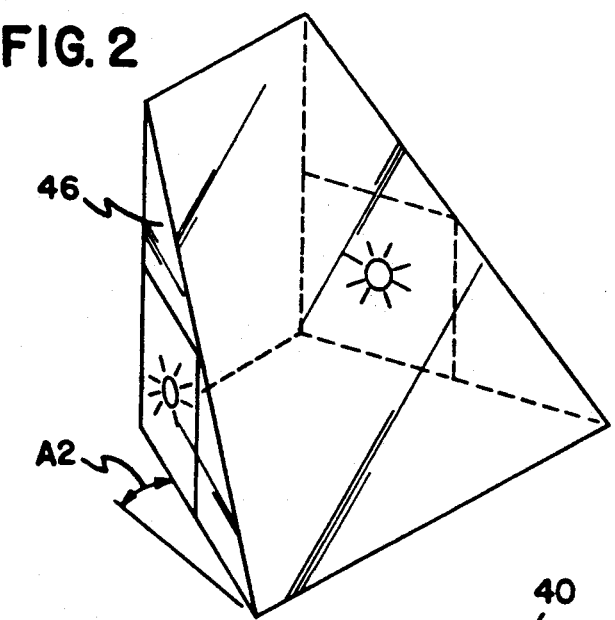
FIG. 2 is a perspective view of the finger prism shown in FIG. 1.
Figure 3:
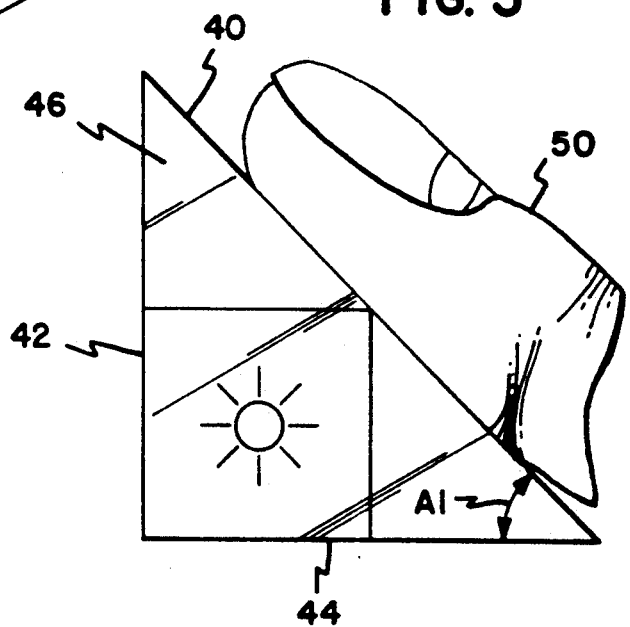
FIG. 3 is a side view of the finger prism shown in FIG. 2.
Figure 4:
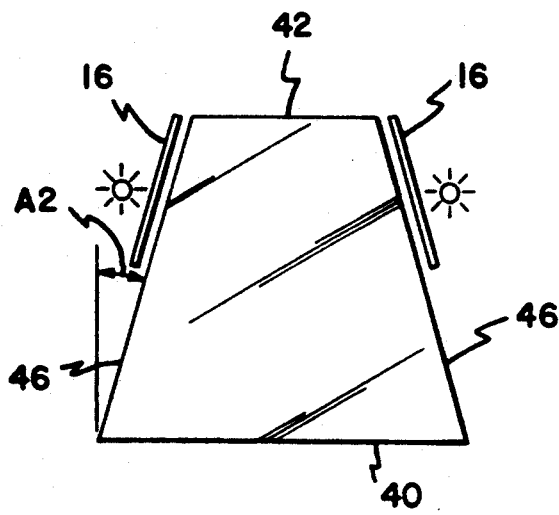
FIG. 4 is a top view of the finger prism shown in FIG. 2.

Optical devices such as finger prism 14 are well known and disclosed, for example, in McMahon U.S. Pat. No. 3,975,711; White U.S. Pat. No. 3,200,701 and Fishbine et al., U.S. Pat. Nos. 4,792,226, 4,811,414 and 4,933,976. These devices use the optical principle of total internal reflection. When a finger is positioned on finger receiving surface 40 (a planer surface in the preferred embodiment but a curved surface could be used), an optical image of the ridge and valley pattern on the surface of the finger (i.e., the fingerprint) is propagated from image propagation surface 42. Finger prism 14 is best described with reference to FIGS. 2–4. Finger prism 14 is an optical device fabricated of a light propagating material, such as plastic, glass or a combination thereof, which is characterized by an index of refraction. As shown, finger prism 14 has a sloping upper surface or finger receiving surface 40 and a rear or image propagating surface 42. Finger prism 14 also includes a bottom surface 44 and two side surfaces 46. Illumination is provided on side surfaces 46 by illumination source 16. In the preferred embodiment, illumination source 16 consists of light-emitting diodes attached to side surfaces 46 of finger prism 14. Bottom surface 44 is coated with an opaque material such as black paint. Finger prism 14 has overall dimensions such that finger receiving surface 40 can receive and image at least one finger 50. Image propagating surface 42 is perpendicular to bottom surface 44. In one preferred embodiment in which finger prism 14 is manufactured of acrylic material, A1 is 45° and A2 is 20°. Finger prism 14 is designed to utilize the optical principle of frustration of total internal reflection. These optical principles are described in Fishbine et al. U.S. Pat. No. 4,811,414 which is hereby incorporated by reference. These properties result in a visual fingerprint image of a finger placed on image receiving surface 40 being propagated through image propagation surface 42. The fingerprint image has "light" areas corresponding to ridges of the fingerprint and "dark" areas corresponding to valleys of the fingerprint. Other means or optical devices which provide fingerprint images can also be used.

Image recorder 18 is mounted with respect to finger prism 14 and configured in such a manner that its field of view encompasses the entire image propagation surface 42. Image recorder 18 continuously images fingerprint images through its objective lens onto its image recording media resulting in an image representative of the light reflected from the parts of the finger 50 in contact with the image receiving surface 40. The recorded image looks like the photographic negative of the fingerprint image. In the preferred embodiment, image recorder 18 is a video camera that continually images fingerprint images through its objective lens, and generates frames of video signals representative thereof. Any commercially available video cameras can be used. In the preferred embodiment image recorder 18 is a Model XC-77 video camera manufactured by Sony Corporation. Alternatively, any type of electronic camera or imager such as an electronically shuttered CCD array or electrophotographic recording device can be used.

The video signal output of image recorder 18 can be viewed on video monitor 26. In the preferred embodiment, video monitor 26 is a Casio 3 inch LCD monitor. The video signal output of image recorder 18 is also wirelessly transmitted by transmitter 30 to a mobile unit (not separately shown). When the operator desires to "capture" a fingerprint image being previewed on video monitor 26, the operator will actuate a key on terminal 28 which generates a signal transmitted by transmitter 30 to the mobile unit that capture and processing of the fingerprint image should be initiated. In the preferred embodiment, terminal 28 has a dual-tone multifrequency (DTMF) keypad. Upon receiving the signal from terminal 28 the mobile unit digitizes and processes the fingerprint image in accordance with methods described in U.S. Pat. Nos. 4,811,414 and 4,933,976. After image processing and compression in the mobile unit, the image can be transmitted wirelessly to a base unit at a central facility, such as a police station, for identity verification using an automated fingerprint identification system such as the FBI's National Crime Information Center Network.

Video camera 20 is a standard video camera that continuously receives images through its objective lens, and generates frames of video signals representative thereof. Commercially available video cameras using conventional rasters and scanning rates can be used. In the preferred embodiment of system 10, video camera 20 is a standard 8 mm video camera Model XC-77 manufactured by Sony Corporation. Any commercially available video camera capable of obtaining a full face or "mug shot" image would be suitable. The video signals generated by video camera 20 may be previewed on video monitor 26 and wirelessly transmitted by transmitter 30 to the mobile unit (not separately shown). When the operator viewing the image in video monitor 26 desires to capture a "mug shot" image, the operator will actuate a key on terminal 18 which sends a signal via transmitter 30 to the mobile unit instructing the mobile unit to capture the image utilizing standard digitizer or frame grabber technology. Video camera 20 may also be connected to a microphone 24 and be provided with an illumination source 22. Video camera 20 may also optionally be used to videotape a person suspected of driving while under the influence of alcohol or drugs. In this situation the video signal transmitted by transmitter 30 to the mobile unit can be recorded on a video tape recorder attached to the mobile unit.

In the preferred embodiment wireless transmitter 30 and the corresponding receiver in the mobile unit use radio frequency transmission. But any other wireless transmission means such as microwave or infrared transmission could be utilized.

Although the present invention has been described with reference to the preferred embodiments, those skilled in the art will recognize that changes may be made in the form and detail without departing from the spirit and scope of the invention.

What is claimed is:

1. A portable apparatus for identification verification, comprising:
    image capturing means for capturing a mug shot image;
    fingerprint scanning means for the capturing live scan fingerprint images, wherein the scanning means comprises image propagation means for propagating the fingerprint image and image recording means for recording the propagated fingerprint image; and
    terminal means, connected to said image capturing means and said fingerprint scanning means, for selecting an image from a group of images including the mug shot image and the captured fingerprint image, wherein the terminal means comprise image transmission means for transmission of the mug shot image and the recorded fingerprint images to a mobile unit.

2. The apparatus of claim 1 wherein said fingerprint scanning means further comprise a contact surface adapted to receive a finger thereon.

3. The apparatus of claim 1 wherein said fingerprint scanning means further comprise a prism for receiving contact from one or more fingers and for propagating images of said fingers.

4. The apparatus of claim 3 wherein said prism further includes means for illuminating said fingers.

5. The apparatus of claim 4 wherein said means for illuminating said fingers comprises light emitting diodes affixed to said prism.

6. The apparatus of claims 4 or 5 wherein said prism includes a reflective coating on all surfaces except the finger receiving surface, image propagating surface and portions of other surfaces used for illuminating said fingers.

7. The apparatus of claim 3 wherein said image recording means is an electronically shuttered CCD array.

8. The apparatus of claim 3 wherein said image recording means is an electrophotograhic recording system.

9. The apparatus of claim 3 wherein said image recording means is a video camera.

10. The apparatus of claim 1, or 3 wherein said transmission means is a radio frequency transmitter.

11. The apparatus of claim 1 wherein said terminal means further comprise display means for displaying the mug shot image and the recorded fingerprint images.

12. The apparatus of claim 1 wherein said image capturing means includes a microphone.

13. The apparatus of claim 1 wherein said image capturing means includes an illumination source.

14. The apparatus according to claim 1, wherein the image transmission means comprise means for wireless transmission of the mug shot image and the recorded fingerprint image to a mobile unit.

15. A portable apparatus for identification verification, comprising:
    a video camera which can be used to capture a mug shot image;
    an optical fingerprint scanner, the fingerprint scanner comprising means for capturing a live scan fingerprint image, wherein the capturing means comprise image propagation means for propagating the fingerprint image and image recording means for recording the propagated fingerprint image; and
    a transmitter connected to said fingerprint scanner, wherein said transmitter is capable of transmitting an image from a group of images including the mug shot image and the recorded fingerprint image.

16. A portable apparatus for identification verification, comprising:
    fingerprint scanning means for the capturing live scan fingerprint images, wherein the scanning means comprises image propagation means for propagating the fingerprint image and recording means for capturing the propagated fingerprint image;
    image capturing means for obtaining an
    image of the person being fingerprinted;
    display means for viewing an image from a group of images including the fingerprinted person's image and the captured fingerprint image; and
    terminal means, connected to said fingerprint scanning, image capturing and display means, for selecting the image to be viewed.

17. The apparatus of claim 16 wherein said fingerprint scanning means further comprise a contact surface adapted to receive a finger thereon.

18. The apparatus of claim 16 wherein said fingerprint scanning means further comprise a prism for receiving contact from one or more fingers and for propagating images of said fingers.

19. The apparatus according to claim 16, wherein the terminal means further comprise transmission means for transmission of the mug shot image and the recorded fingerprint images to a mobile unit.

20. The apparatus according to claim 19, wherein the transmission means comprise means for wireless transmission of the mug shot image and the recorded fingerprint images.

21. A method of verifying the identity of a person, comprising the steps of:
    providing a portable personal identification unit which can be used for field identification of a person, wherein the portable unit comprises:
    first camera means for capturing a mug shot image of the person to be identified;
    fingerprint capture means for propagating a fingerprint image; and
    second camera means for capturing the propagated fingerprint image;
    carrying the unit to a first location;
    capturing, with the first camera means, a mug shot image of the person;

capturing, with the second camera means, a fingerprint image representative of a fingerprint pattern of one of the person's fingers;

transmitting the mug shot image and the fingerprint image to a second location.

22. The method of verifying the identity according to claim 21, wherein the method further comprises the step of comparing the transmitted fingerprint images to stored fingerprint images in an automated fingerprint identification system.

* * * * *